United States Patent
Palmer (10) Patent No.: US 8,116,878 B1
(45) Date of Patent: Feb. 14, 2012

(54) DUAL-RANGE COMPLIANCE VOLTAGE SUPPLY FOR A MULTI-CHANNEL STIMULATOR

(75) Inventor: Logan P. Palmer, Santa Monica, CA (US)

(73) Assignee: Advanced Bionics, Valencia, CA (US)

( * ) Notice: Subject to any disclaimer, the term of this patent is extended or adjusted under 35 U.S.C. 154(b) by 992 days.

(21) Appl. No.: 12/057,891

(22) Filed: Mar. 28, 2008

Related U.S. Application Data (62) Division of application No. 10/459,040, filed on Jun. 11, 2003, now Pat. No. 7,519,428.

(60) Provisional application No. 60/388,731, filed on Jun. 14, 2002.

(51) Int. Cl.
*A61N 1/32* (2006.01)

(52) U.S. Cl. .......................................... 607/72

(58) Field of Classification Search .................... 607/74, 607/72, 148, 55–57, 25, 2, 66–68
See application file for complete search history.

(56) References Cited

U.S. PATENT DOCUMENTS

| | | | |
|---|---|---|---|
| 4,532,930 A | 8/1985 | Crosby et al. | |
| 4,592,359 A * | 6/1986 | Galbraith | 607/57 |
| 4,931,795 A | 6/1990 | Gord | |
| 4,990,845 A | 2/1991 | Gord | |
| 5,344,387 A | 9/1994 | Lupin | |
| 5,522,865 A | 6/1996 | Schulman et al. | |
| 5,531,774 A | 7/1996 | Schulman et al. | |
| 5,601,617 A | 2/1997 | Loeb et al. | |
| 5,603,726 A | 2/1997 | Schulman et al. | |
| 5,776,172 A | 7/1998 | Schulman et al. | |
| 5,824,022 A | 10/1998 | Zilberman et al. | |
| 5,876,425 A | 3/1999 | Gord et al. | |
| 5,917,346 A | 6/1999 | Gord | |
| 5,938,691 A | 8/1999 | Schulman et al. | |
| 5,999,848 A | 12/1999 | Gord et al. | |
| 6,002,966 A | 12/1999 | Loeb et al. | |
| 6,035,237 A | 3/2000 | Schulman et al. | |
| 6,157,861 A | 12/2000 | Faltys et al. | |
| 6,181,969 B1 | 1/2001 | Gord | |
| 6,219,580 B1 | 4/2001 | Faltys et al. | |
| 6,799,070 B2 | 9/2004 | Wolfe et al. | |
| 7,519,428 B1 * | 4/2009 | Palmer | 607/57 |
| 2005/0085873 A1 | 4/2005 | Gord et al. | |

FOREIGN PATENT DOCUMENTS

WO WO-01/08282 2/2001

* cited by examiner

*Primary Examiner* — George Evanisko (74) *Attorney, Agent, or Firm* — AdvantEdge Law Group, LLC (57) ABSTRACT

In accordance with an aspect of the present systems and methods, there is provided a multi-channel stimulator having a common supply voltage, the stimulator having an electrical circuit with a dual-range compliance voltage supply such that each channel of the multi-channel stimulator is configured to be selectable among two compliance voltages. Channels which can operate at half or less than half compliance voltage can operate in the lower voltage range and thereby achieve energy savings. The stimulator can be switched between a high and low compliance voltage in a bipolar or a monopolar electrode configuration.

7 Claims, 6 Drawing Sheets

DUAL-RANGE COMPLIANCE VOLTAGE SUPPLY FOR A MULTI-CHANNEL STIMULATOR

RELATED APPLICATIONS

The present application is a divisional application of U.S. patent application Ser. No. 10/459,040, filed Jun. 11, 2003, which application claims the benefit of U.S. Provisional Patent Application Ser. No. 60/388,731, filed Jun. 14, 2002. Both applications are incorporated herein by reference in their entireties.

BACKGROUND

Multi-channel stimulators are used in a number of implantable or partially implantable medical devices. Some of these devices include spinal cord stimulators and partially implantable and fully implantable hearing devices.

One challenge with such stimulators is keeping power usage to a minimum to conserve battery life. While increasing battery life may be achieved by extending the size of the battery, that runs counter to the goal of reducing the overall device size which is determined partly by battery size. Conservation of energy in implantable, battery operated devices is an important design goal in order to reduce the overall size of the device. Additionally, given a fixed battery capacity and size, conservation of energy is further desired to prolong the life of the battery.

A cochlear device for restoration of hearing is an exemplary device which uses a multi-channel stimulator. Such a device may be fully implantable or partially implantable. In a partially implantable device, there can be two components, an external component containing the battery and an implantable component which contains additional circuitry for processing the stimulation protocol. The power consumed in this processing circuitry, in addition to the power dissipated through the stimulation leads and electrodes, can be substantial.

It is desirable to improve the efficiency of such a device so that the battery can be recharged with less frequency. Frequent recharging is inconvenient to the user and, moreover, causes the rechargeable battery to reach its end of life more quickly.

A multi-channel spinal cord stimulator for treatment of intractable pain is an exemplary, fully implantable device, wherein the battery is contained inside the device. In this application, prolonging battery life is very important to defer surgery to replace the device.

Conventional multi-channel stimulators can be designed to have a single compliance voltage supply that is common to each channel. A "compliance voltage" is the voltage necessary to drive a desired (e.g. programmed) stimulating current through an electrode, which stimulation current is sufficient to cause excitable tissue to be stimulated at the desired intensity. The compliance voltage varies with the impedance of the electrode-tissue interface and the stimulation threshold of the tissue being stimulated.

Each channel in a multi-channel stimulator has varying compliance voltage requirements because the electrodes interfacing with the body tissue provide varying electrode/tissue impedances. For purposes of discussion, the electrode/tissue impedance, which is a combination of resistance and capacitance will be hereinafter referred to as a simple resistance. Although compliance voltage varies at each channel, in conventional multi-channel stimulators, a common compliance voltage is used for each of the channels. This electrical configuration wastes available battery power since it is unnecessary to have each channel operate at the same compliance voltage. In particular the compliance voltage is set to the highest setting required to satisfy the channel having the highest requirement. The other channels are also set to the same compliance voltage even though these other channels may actually need a smaller maximum compliance voltage.

SUMMARY

The systems and methods described herein provide a device for reducing the unnecessary dissipation of energy in a multi-channel stimulator. In this manner, battery life may be prolonged.

In accordance with an aspect of the present systems and methods, there is provided an electrical circuit device that allows each stimulation channel to be independently selectable between high and low compliance voltage supplies. Channels which can operate at half or less than half compliance voltage can operate in the lower range to optimize power usage and thereby achieve energy savings.

The stimulation circuit for a channel in a multi-channel stimulator has a common voltage power supply with a selectable, dual-range compliance voltage for each channel. The stimulation circuit comprises: first and second electrode contacts, first and second current sources (defined as the first, dual current sources), wherein the first current source has a first connection and a second connection, the second current source has a third connection and a fourth connection and the second and fourth connections are electrically connected. The stimulation circuit further comprises a third and fourth current sources (defined as the second, dual current sources), wherein the third current source has a fifth connection and a sixth connection, the fourth current source has a seventh connection and an eighth connection, wherein the sixth and eighth connections are electrically connected. The stimulation circuit further comprises a bypass switch which, when in a first, closed position (but open to the stimulation circuit), bypasses the third and fourth current sources and electrically connects the second electrode contact to ground, thereby providing a low compliance voltage supply mode and, when the bypass switch is in a second, closed position, permits the first and third current sources to operate together in a push pull configuration and the second and fourth current sources to operate together in a push-pull configuration, thereby providing a high compliance voltage supply mode. The first current source and second current source provide opposite current flow in the stimulation circuit and operate such that only one of the first or second current source operates at one time. The third current source and fourth current source provide opposite current flow through the circuit and operate such that only one of the third or fourth current source operates at one time.

It is a feature of the systems and methods described herein to provide electrical circuits that provide dual-range compliance voltages for a bipolar electrode configuration.

It is a further feature of the systems and methods described herein to provide electrical circuits that provide dual-range compliance voltages for a monopolar electrode configuration.

It is yet another feature of the systems and methods described herein to provide electrical circuits that permit uniphasic or biphasic stimulation of neural cells.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Multi-channel stimulators are used in various implantable medical devices. For example, such multi-channel stimulators can be found in spinal cord stimulation devices for treating intractable pain and cochlear devices for restoration of hearing in the profoundly deaf. As an exemplary application of the present systems and methods, the systems and methods described herein will be discussed in the context of use in a cochlear implant device. Details associated with the operation of a typical cochlear implant system may be found in one or more of the following U.S. patents, each of which is incorporated herein by reference: U.S. Pat. Nos. 6,157,861; 6,002,966; 5,824,022; 5,603,726; 5,344,387; and 4,532,930.

Figure 1:
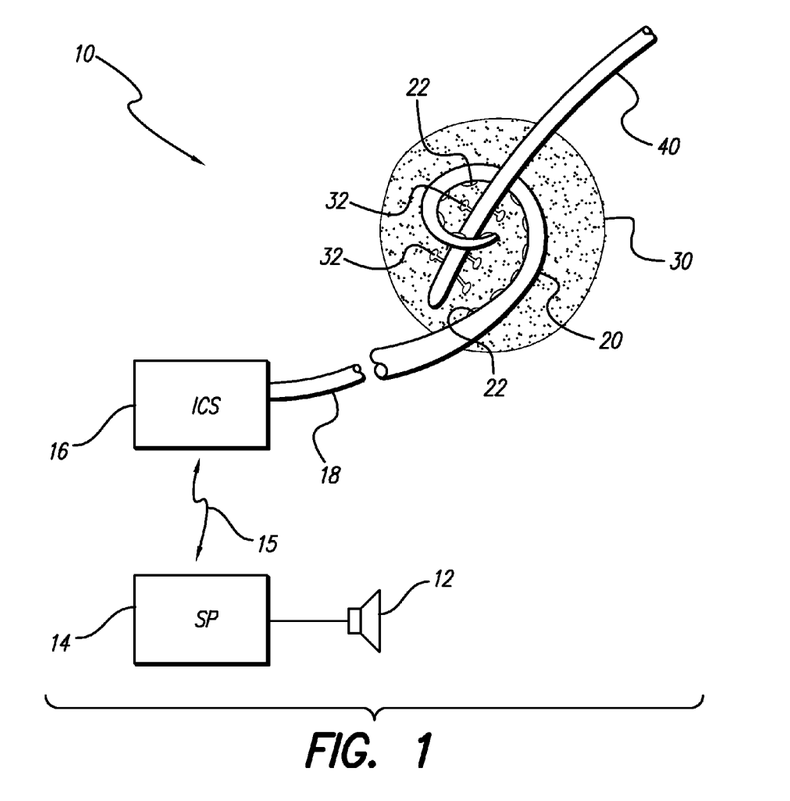
FIG. 1 depicts a functional block diagram of a multi-channel, cochlear stimulation system.

Before describing the present systems and methods, it will be helpful to review the operation of a typical cochlear stimulation system. A representative cochlear stimulation system 10 is illustrated in FIG. 1. A microphone 12 senses acoustic waves and converts such sensed waves to an electrical signal. The electrical signal is then processed in an appropriate manner by a speech processor (SP) 14. Such processing may include dividing the signal into different frequency bands and generating an appropriate stimulation control signal for each frequency band. The stimulation control signal(s) is passed on to an implantable cochlear stimulator (ICS) 16 via a radio-frequency communications link 15. The ICS 16 is connected to an electrode array 20. The electrode array 20 is inserted into a cochlea 30. (Note, that the representation of the cochlea 30 shown in FIG. 1 is meant only as a schematic representation.)

The electrode array 20 includes a plurality of spaced-apart electrode contacts 22 thereon. Each electrode contact 22 is electrically connected to the electrical circuitry within the ICS 16 by way of a lead 18, which lead 18 has a plurality of electrical wire conductors embedded therein as is known in the art. The ICS, in response to the control signal(s) received from the SP 14, generates an electrical stimulation current on selected groupings of the electrode contacts 22.

The cochlea 30, as is well known in the art, comprises a snail shaped member having three parallel ducts that spiral around its center bony region, known as the modiolus. One of the spiraling parallel ducts within the cochlea is the scala tympani. The center bony region, or modiolus, is where ganglion nerve cells 32 are located. Each of the ganglion cells 32 is coupled to the auditory nerve 40, which connects to the brain.

It is the function of the cochlear stimulation system 10 to electrically stimulate the ganglion cells 22 with electrical stimulation current representative of the acoustic waves sensed by the microphone 12. In order to achieve this function, the electrode array 20 is inserted into the scala tympani so that the electrode contacts 22 encircle the modiolus and ganglion cells 32. Electrical stimulation current flows between selected electrode contacts 22 and hence stimulates the ganglion cells 32 near the selected electrode contacts, as controlled by the ICS 16 in accordance with a programmed or selected speech processing strategy. The speech processing strategy is defined by the control signals received from the SP 14. The control signals are modulated by the acoustic waves sensed by the microphone 12, thereby causing the stimulation current to stimulate appropriate ganglion cells as a function of the sensed acoustic waves. For example, low frequency acoustic waves cause ganglion cells near the apical tip of the cochlea to be stimulated, whereas high frequency acoustic waves cause ganglion cells near the basal region of the cochlea to be stimulated.

Stimulation of the ganglion cells can be accomplished using two electrode configuration modes. One electrode configuration mode is a "bipolar mode," which uses two electrode contacts 22 positioned relatively close to each other. In this mode, the load resistance appears between the two electrode contacts 22. The load resistance is contributed to by the interface between the tissue and electrode contacts 22 and the tissue itself between the electrode contacts.

Another electrode configuration is a "monopolar mode," which employs one of the electrode contacts 22 in the electrode array and an indifferent electrode that is relatively distant from the electrode contacts 22. In some cases, the indifferent electrode can be the exterior container (the "case") of the ICS, which container can be made from a biocompatible, electrically conductive metal such as titanium. In the monopolar electrode configuration, the load resistance is contributed to by the interface between the electrode contact 22 and tissue, the interface between the indifferent electrode and tissue, and the tissue itself between the electrode contact and the indifferent electrode.

There are two stimulus modes: a uniphasic stimulus and a biphasic stimulus mode. A uniphasic stimulus provides current flow in only one direction through an electrode. A biphasic stimulus, however, provides current flows in both directions through an electrode within a relatively short time period. It is thought that uniphasic stimulation may cause charges to accumulate in the tissue near the stimulating electrode and thereby cause injury to this tissue. In addition, it is also believed that uniphasic stimulation can cause premature degradation of the electrodes. Therefore, most conventional multi-channel stimulators, including ones for cochlear stimulators, use some form of biphasic stimulation.

Figure 2:
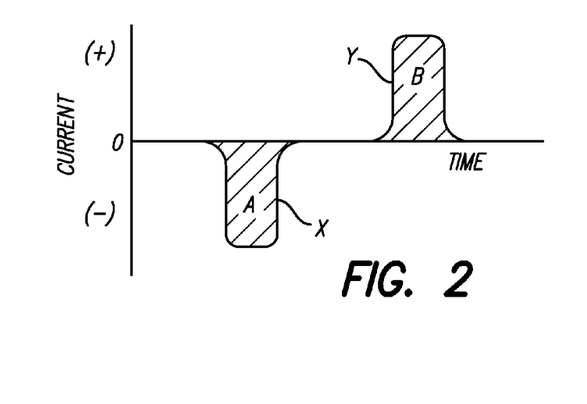
FIG. 2 shows a graph of charged-balanced, biphasic stimulation delivered through a stimulating electrode contact.

FIG. 2 shows a graph of a biphasic stimulus as a function of time. Stimulus pulse waveforms X and Y are individually uniphasic. But considered together, they are biphasic because the flow of stimulation current through an active electrode is in both directions. A particular biphasic stimulation in which an equal quantity of electrical charge flows in both directions through an electrode is termed a "charged-balanced," biphasic stimulation. A charge balanced stimulation can be achieved by ensuring that the flow of charge in both directions through a stimulating electrode is equal over time. As represented in the graph of FIG. 2, the accumulation of charge is represented by the area (A) and area (B) above and below the zero current flow line, respectively. In this graph the areas above and below the zero line should be equal over a period of time in order to achieve charge balancing. Such charge balancing is believed to prevent injury to cells which are near the stimulating electrode and, furthermore, prevent the stimulating electrode from degrading prematurely. For these reasons, conventional, multi-channel stimulators for cochlear implants and spinal cord stimulation generally employ charged balanced stimulation regimes.

Figure 3:
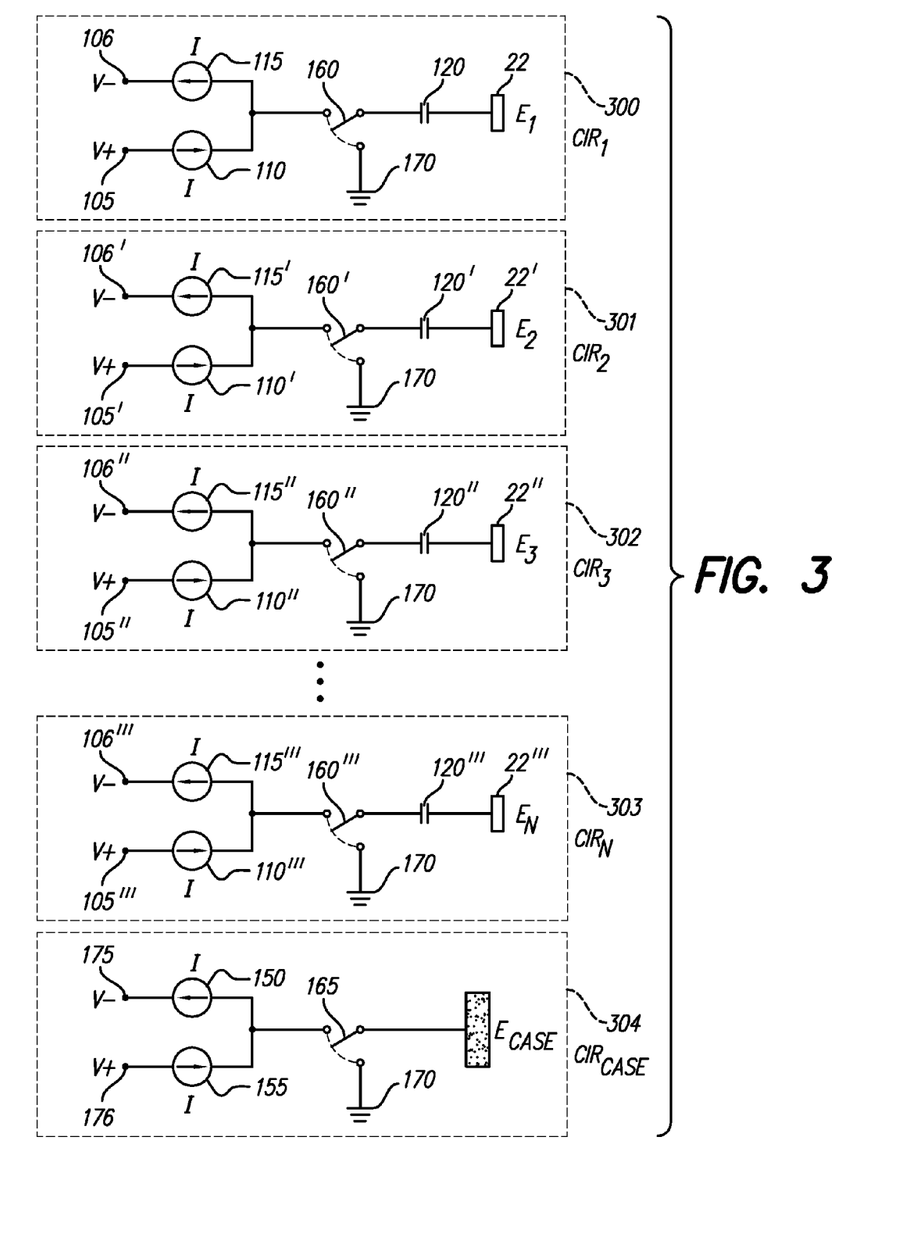
FIG. 3 shows a partial view of a multi-channel stimulation output circuitry depicting N number of electrodes and one case (housing) electrode.

FIG. 3 shows, in accordance with the present systems and methods, a circuit diagram of a portion of a multi-channel stimulator circuit connected to N number of electrodes, $E_1$ . . . $E_N$, and a case or housing electrode $E_{CASE}$. Each partial circuit, designated as $CIR_1$, $CIR_2$, $CIR_3$ . . . $CIR_N$ or $CIR_{CASE}$, has dual current sources electrically connected to its respective electrode, $E_1$, $E_2$, $E_3$ . . . $E_N$ or $E_{CASE}$. Partial circuits $CIR_1$, $CIR_2$, $CIR_3$ . . . $CIR_N$ also include a D.C. blocking capacitor, 120, 120' 120" or 120'". In addition, each partial circuit has a bypass switch 160, 160', 160", 160'" or 165 for bypassing dual current sources and, instead, connecting the stimulation circuit to ground 170 ("first closed position") or electrically connecting the stimulation circuit to the dual current sources ("second closed position"). Generally, each partial circuit, $CIR_1$, $CIR_2$, $CIR_3$ . . . $CIR_N$ of a multi-channel stimulator, is identical. $CIR_{CASE}$, however, is different because the device case or housing, which may act as an indifferent electrode, generally has a larger surface area than a stimulating electrode and, moreover, does not include a D.C. blocking circuit since $CIR_{CASE}$ may be used in combination with one of the partial circuits, $CIR_1$, $CIR_2$, $CIR_3$ . . . $CIR_N$, each of which already includes a D.C. blocking capacitor, 120, 120', 120" or 120'", sufficient to prevent delivery of direct current to stimulated tissue.

A complete stimulation circuit is formed by combining two partial circuits selected from the set $CIR_1$, $CIR_2$, $CIR_3$ . . . $CIR_N$ and $CIR_{CASE}$. For example, $CIR_1$ combined with $CIR_3$ forms a bipolar stimulation circuit having two electrodes $E_1$ and $E_3$. Another example is the combination of $CIR_2$ and $CIR_3$ having two electrodes $E_2$ and $E_3$ and forming another bipolar stimulation circuit. A monopolar, stimulation circuit may be formed by combining partial circuit, $CIR_{CASE}$, with one of the circuits in the set, $CIR_1$, $CIR_2$, $CIR_3$ . . . $CIR_N$. In such an instance, the device case or housing functions as an indifferent electrode, $E_{CASE}$, and one selected electrode among the set, $E_1$, $E_2$, $E_3$ . . . $E_N$, acts as the stimulating electrode. When two partial circuits are thus combined to form a complete stimulating circuit, two sets of dual current sources are in the stimulation circuit. In operation, however, only two current sources may operate at any one time. For example, current sources 115 and 110' may operate together at one time to produce stimulus current waveform X in FIG. 2, as measured at $E_1$. Or current sources 110 and 115' may operate together to produce stimulus current waveform Y in FIG. 2, as measured at $E_1$. Such arrangement of paired current sources is termed a "push-pull" arrangement.

Figure 4:
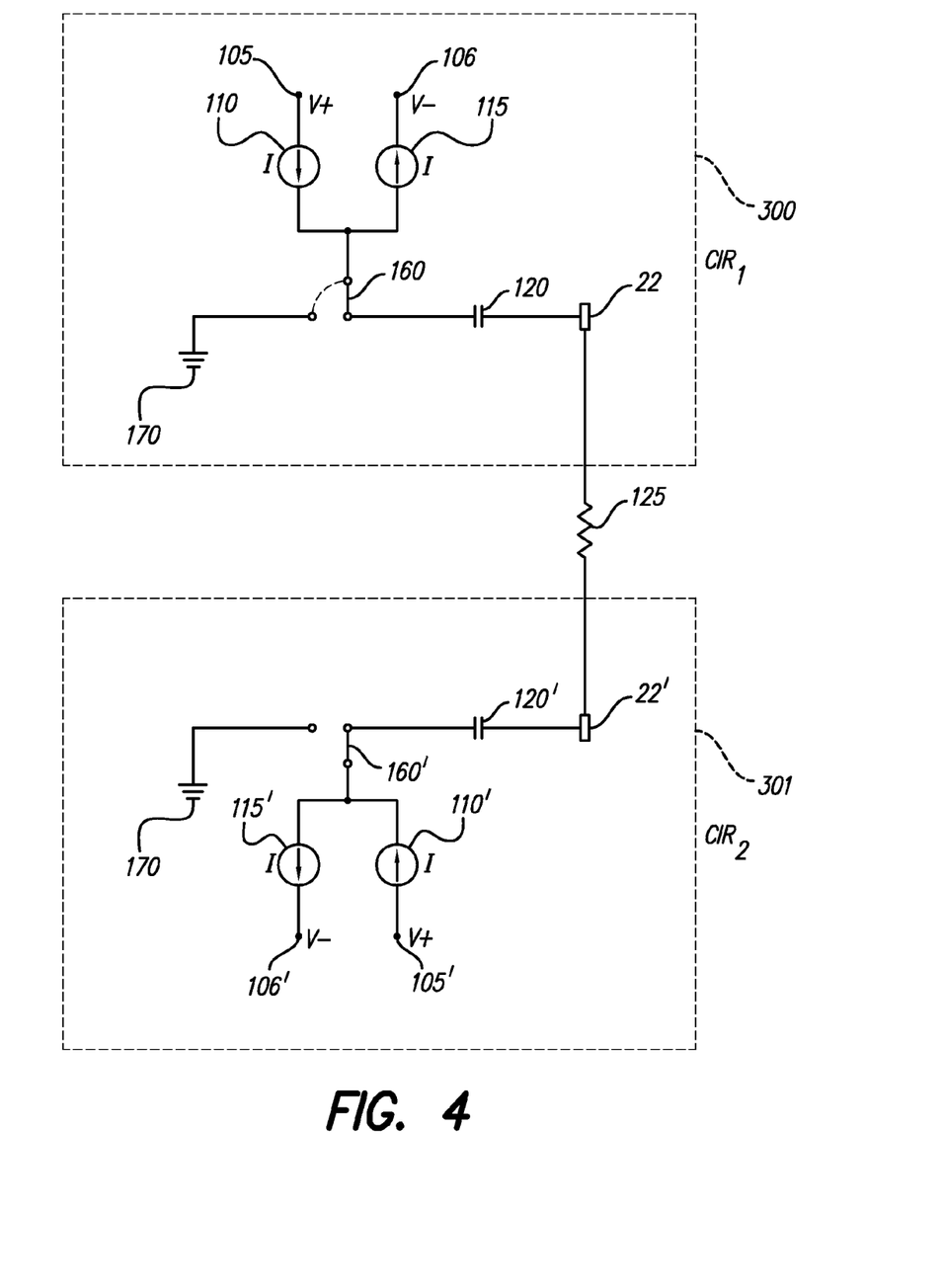
FIG. 4 shows, in accordance with the present systems and methods, a schematic diagram of an electrical stimulation circuit, comprised of two partial circuits, and which electrical stimulation circuit uses a push-pull, pair of current sources in high compliance voltage mode and delivers stimulation into a bipolar electrode configuration.

FIG. 4 shows, in accordance with the present systems and methods, a schematic circuit diagram of a complete stimulation circuit which utilizes a push-pull pair of current sources in a high compliance voltage mode. It can be seen that $CIR_1$ and $CIR_2$, shown in FIG. 3, may be combined together to provide a complete bipolar circuit, as shown in FIG. 4. Rails 105, 106 and 105', 106' provide electrical connection points for a common supply voltage. FIG. 4 shows, for purposes of illustration, a rail 105 which can be connected to a voltage of V+relative to ground and rail 106' which can be connected to a voltage of V−. To provide current flowing in the opposite direction through the stimulation circuit, rail 106 can be connected to a voltage V− and rail 105' can be connected to a voltage V+.

As shown in FIG. 4, electrode contacts 22 and 22' may be part of an electrode array, for example, as depicted in FIG. 1. The complete stimulation circuit has two pairs of dual current sources, two D.C. blocking capacitors 120, 120' and two bypass switches 160, 160', either of which may be used to bypass dual current sources 115, 110 or 115', 110' and connect, instead, to ground 170. Resistor 125 simplistically represents the load resistance presented by the body tissue between the two electrode contacts 22 and 22'. The four current sources may be current mode, digital-to-analog converters (DACs). Current sources 115 and 110' operate together in a "push pull" arrangement to direct current flow in one (uniphasic) direction through the circuit and through the electrode contacts 22 and 22' such that electrode contact 22 functions as a cathode and electrode contact 22' functions as an anode. Similarly, in a different time interval, the pair of current sources 110 and 115' operate together to direct current flow in the opposite direction through the stimulation circuit and through the electrode contacts 22 and 22', such that electrode contact 22' is a cathode and electrode contact 22 is an anode. It can be appreciated that current sources 110 and 115' are operating only when current sources 115 and 110' are turned off and vice versa. A software program may be used to dynamically turn on and off the push pull pairs of current sources in timed intervals.

It can be seen that by turning alternately on and off, in timed intervals, the push-pull pairs of current sources 110, 115' and 115, 110', the stimulation current flow through the electrode contacts 22 and 22' can be made biphasic, as shown in FIG. 2. An interval timer may enable current sources 110 and 115' together in one timed interval, while current sources 115 and 110' are disabled, then, in the next interval, current sources 115 and 110' may be enabled together, while current sources 110 and 115' are disabled, and so on.

Capacitors 120 and 120' are internal, blocking capacitors which function to block direct current. These blocking capacitors prevent the possible occurrence of direct current being applied through electrode contacts 22 and 22' which can harm tissue near these contacts. As shown in FIG. 4 bypass switch 160 is in a "second closed" position to connect the stimulation circuit to the dual current sources 110 and 115. Similarly, bypass switch 160' is in a "second closed" position connecting the stimulation circuit to the dual current sources 110' and 115'. With the bypass switches 160 and 160' thereby in such positions, the voltage difference or the compliance voltage between rails 105' and 106 is effectively V minus −V=2V, which is the high compliance voltage mode. The voltage difference or compliance voltage between rails 105 and 106' is similarly V minus −V=2V. In the ideal circumstance, the stimulation circuit can supply a maximum current of Imax into a tissue resistance of R=2V/Imax and an operating power consumption of P=2V*$I_{stim}$, where $I_{stim}$ is the stimulation current delivered to body tissue at a specific time. Switching the bypass switch 160' between a first, closed position, i.e., connecting the stimulation circuit to ground 170, and a second, closed position, connecting the stimulation circuit to dual current sources 115' and 110' (while switch 160 remains in a second, closed position, connecting dual current sources 110 and 115), as well as enabling and disabling current source pairs, (110, 115') and (115 and 110'), can be accomplished with appropriate software programmable controls. It can further be seen that the same effect may be accomplished by holding bypass switch 160' in a second, closed position, which connects dual current sources 115' and 110' to the stimulation circuit, while bypass switch 160 selects between connecting the stimulation circuit to ground 170 or dual current sources 110 and 115.

Figure 5:
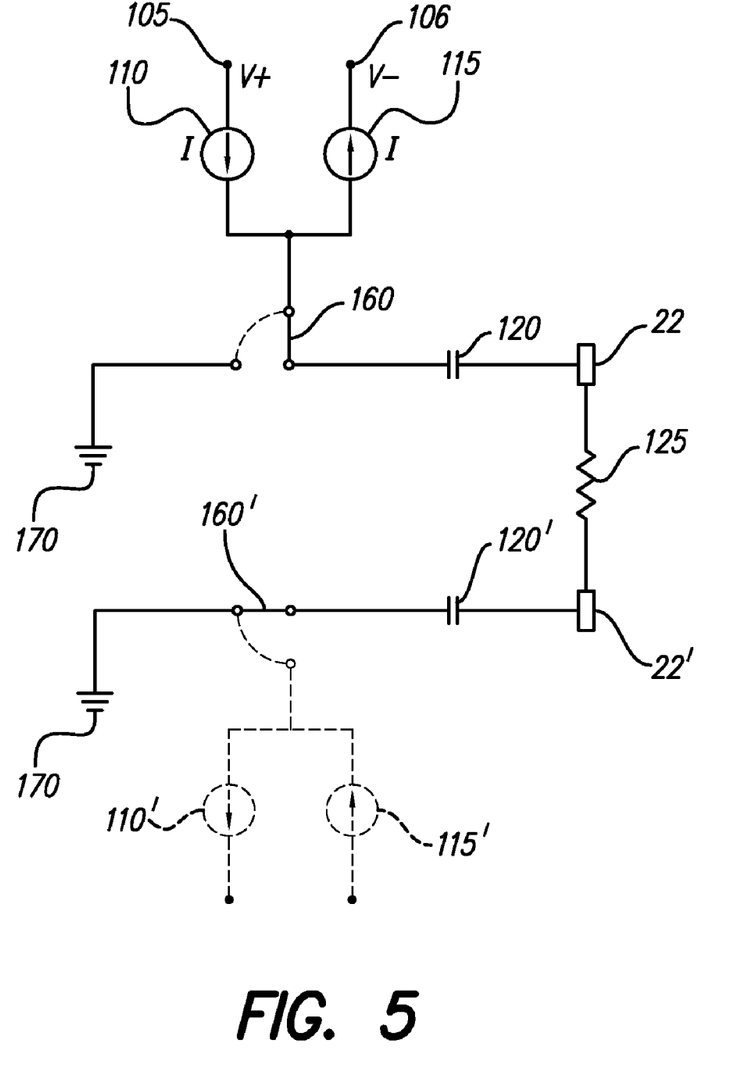
FIG. 5 shows, in accordance with the present systems and methods, the identical electrical stimulation circuit depicted in FIG. 3, except with one switch bypassing one set of dual current sources, thereby activating the low compliance voltage mode (in a bipolar electrode configuration)

FIG. 5 shows, in accordance with the present systems and methods, an identical circuit diagram as provided in FIG. 4, except that the stimulation circuit is switched to a low compliance voltage mode. In this mode, the bypass switch 160' connects the stimulation circuit to ground 170 and, hence, bypasses the dual current sources 110' and 115', which can be turned off, as they are not needed. Bypass switch 160 is placed in the second, closed position to permit dual current sources 110 and 115 to be connected to the stimulation circuit. The compliance voltage of the stimulation circuit as seen from rail 105 to ground 170 is V−0=V and from the ground to rail 106 is 0 minus −V=V. In the ideal circumstance, the circuit can supply a maximum current Imax into a tissue resistance of R=V/Imax. The operating power consumption of the stimulation current is P=V*$I_{stim}$ because the compliance voltage is halved from 2V to V. The maximum load resistance through which a given $I_{stim}$ is supplied is also halved.

In operation, a biphasic stimulation with the circuit of FIG. 5 may be delivered by applying V− to rail 106 and enabling current source 115 in one interval, while current source 110 is turned off. This provides a uniphasic, stimulus pulse through electrode contacts 22 and 22' in one circuit direction, for instance, as shown by curve X in FIG. 2. Then, in the next interval, current source 115 is disabled and, at the same time, current source 110 is enabled, while rail 105 has V+applied, providing another uniphasic, stimulus pulse but in the opposite direction through the circuit, for example, shown as curve Y in FIG. 2. These two uniphasic pulses, flowing through the circuit in opposite directions at different times, may be combined to provide a charged-balanced, biphasic stimulation regime.

Figure 6:
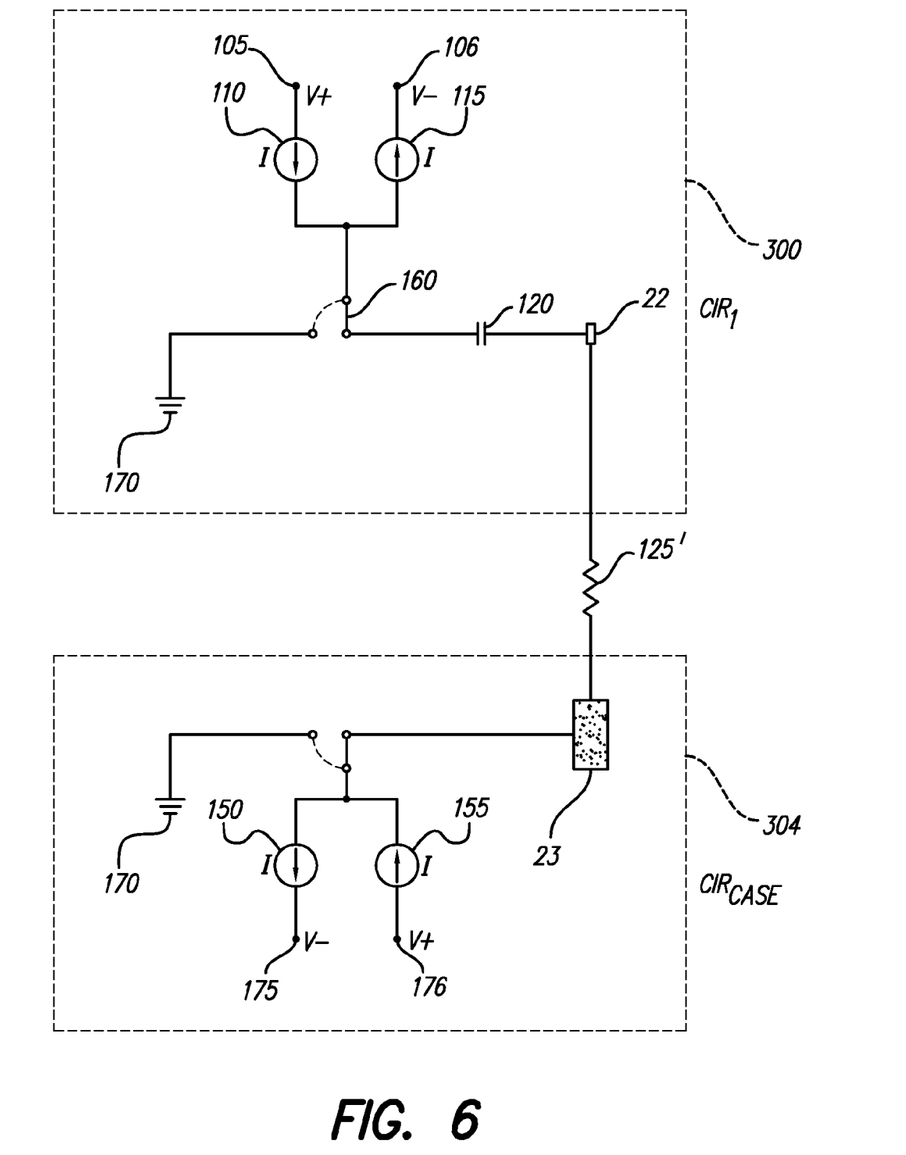
FIG. 6 shows, in accordance with the present systems and methods, a schematic diagram of an electrical stimulation circuit, comprised of two partial circuits, which electrical stimulation circuit utilizes a push-pull, pair of current sources in high compliance voltage mode and delivers stimulation into a monopolar electrode configuration.

FIG. 6 shows, in accordance with the present systems and methods, a schematic diagram of an electrical stimulation circuit which uses push-pull, current sources in a high compliance voltage mode. The circuit delivers current stimulation into a monopolar electrode configuration, where electrode 22 is the active electrode and electrode 23 is the indifferent electrode, usually the case or housing of an implantable medical device. The complete circuit is a combination of two partial circuits $CIR_1$ and $CIR_{CASE}$. $CIR_1$ is connected to the electrode contact 22 via a D.C. blocking capacitor 120. Indifferent case electrode 23 is connected to either ground 170 or dual current sources 150 and 155 via a bypass switch 165. As shown, electrode 23 is not connected to a D.C. blocking capacitor of its own, because partial circuit $CIR_{CASE}$ will always be combined with at least one partial circuit in the set $CIR_1$, $CIR_2$, $CIR_3$ ... $CIR_N$, which already includes a D.C. blocking capacitor. Load resistor 125' represents a simplified resistance provided by the tissue between the electrode 22 and indifferent electrode 23.

In this monopolar electrode configuration, electrode contact 22 is near or in contact with the tissue to be stimulated. Indifferent electrode 23, which is often the medical device case or housing, however, is generally distant from the target tissue and also distant from electrode contact 22.

To enable the high compliance voltage mode (2V), the bypass switch 165 is programmed to the second, closed position. Current source pair 110 and 150 operate together to drive current in one circuit direction, while rail 105 has V+applied and rail 175 has V− applied. Current source pair 115 and 155 work together in a push-pull arrangement to drive current flow in an opposite circuit direction, while rails 106 and 176 have V− and V+voltages applied, respectively.

Figure 7:
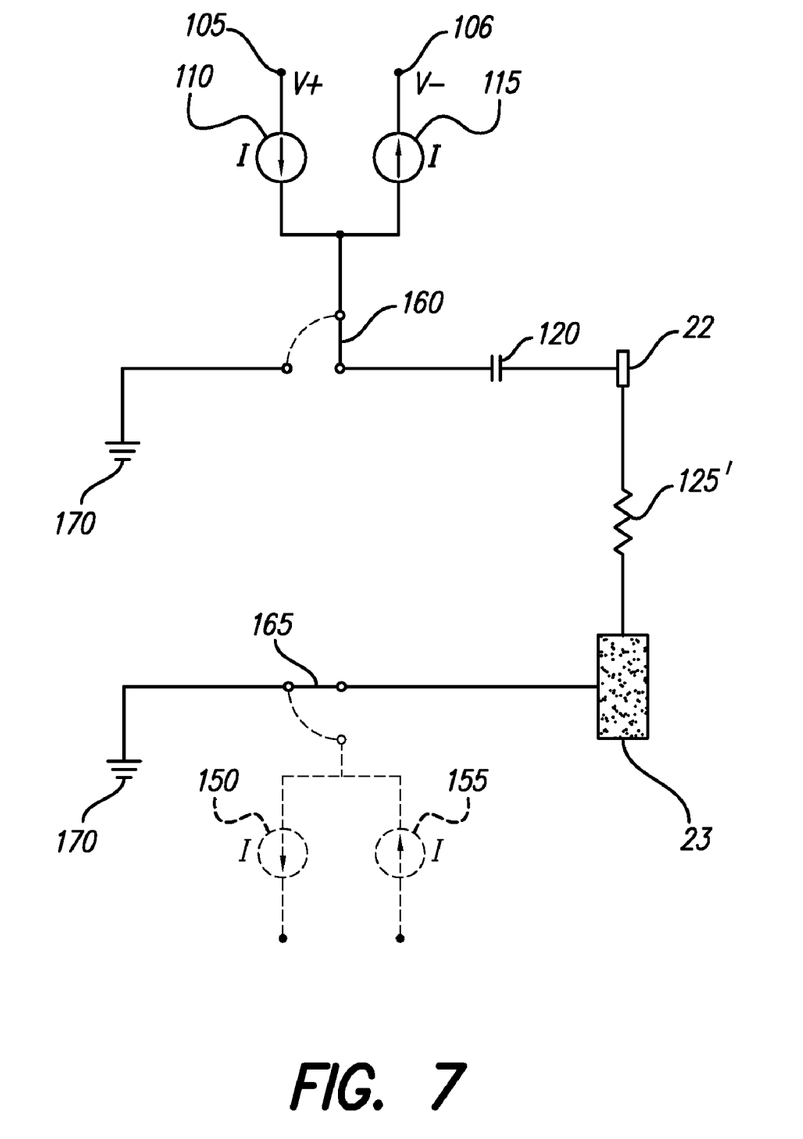
FIG. 7 shows, in accordance with the present systems and methods, the identical electrical stimulation circuit depicted in FIG. 5, except with one switch bypassing one set of dual current sources, thereby activating the low compliance voltage mode (in a monopolar electrode configuration).

FIG. 7 shows, in accordance with the present systems and methods, the identical circuit of FIG. 6, except switched to the low compliance voltage mode (V). The electrode configuration is once again monopolar with electrode contact 22 and indifferent electrode contact 23. To provide the low compliance mode, the bypass switch 165 is in the first, closed position, thereby bypassing dual current sources 150 and 155. Because dual current sources 150 and 155 are not being used, they may be turned off. Alternatively, bypass switch 160 can bypass dual current sources 110 and 115 and connect to ground, while bypass switch 165 connects the stimulation circuit to dual current sources 150 and 155. This latter circuit configuration would also produce a low compliance voltage, monopolar electrode configuration.

Referring to FIG. 3, the voltages at pairs of rails 105, 106'; 106, 105'; 105, 175; and 106, 176 are provided by the common supply voltage. Each of the up to N stimulation circuits (channels) can operate independently and be selected to operate between low and high compliance voltages, as previously described. The bypass switches 160 and 165 may be used to control the compliance mode for each stimulation channel. To provide instantaneous switching between low and high compliance voltage modes, the switches 160 and 165 for each stimulation circuit may be independently and dynamically controlled by software. Dynamic switching does not require user involvement and this instantaneous adjustment of compliance voltages can further optimize the power consumed by each channel.

The present systems and methods thus allows selection of low and high compliance voltage independently for each stimulation channel connected in parallel to a common supply voltage. In this manner each stimulation channel (or stimulation circuit) may be independently switched to use either low or high compliance modes according to the needs of each stimulation channel. The selection of compliance voltage modes may be automatically stored in long-term memory contained in the stimulator. The stimulation threshold data of each stimulation channel (or stimulation circuit) consisting of two electrode contacts or one electrode contact and an indifferent, case electrode may also be stored in memory for later retrieval and used to select whether a stimulation channel should be set to low or high voltage compliance modes.

Stimulation thresholds may differ widely and are a function of differences in the position of an electrode contact relative to the ganglion nerves in the cochlea and to physiological variance in the location of the nerves along the cochlea. Even very slight electrode positional differences can have marked changes in stimulation thresholds.

The stimulation thresholds may be measured in various ways, for example, stimulation current may be applied at the two electrode contacts, e.g., the magnitude of the current (with pulsewidth held constant) may be increased until some indication of nerve firing is noticed or measured. In the case of cochlear stimulation, threshold stimulation may be determined by the perception of sound or, alternatively, the stimulator device may have sensors which can detect nerves firing when they are captured by a stimulus that is at or above stimulation threshold. Once such stimulation threshold is obtained for each channel, this threshold information may be kept in memory and later recalled in order to set each channel (or stimulation circuit) to either a low or high voltage compliance modes. The setting of the voltage compliance mode may be done nearly instantaneously, using dynamic switching.

Each selected channel may be independently set so that low voltage compliance mode may be used whenever possible. The current draw in the low voltage compliance mode may be halved and, thus, energy use can be reduced. Such energy savings may be substantial. Up to a 20 to 25% savings in energy may be achieved, if half of the channels are operated in low voltage compliance mode.

Further, each channel (or stimulation circuit) may provide uniphasic or biphasic stimulation, and selection of monopolar or bipolar electrode configurations.

As an exemplary embodiment, a multi-channel stimulation system for cochlear application has been discussed. It can be appreciated, however, that the present systems and methods may be used with any multi-channel stimulation system having a single common supply voltage and where each channel has a different compliance voltage requirements. For example, a spinal cord stimulator for treating intractable pain can have multiple channels and may have a circuit design which utilizes a common power supply. Such a circuit may be amenable to utilizing a dual range compliance voltage as provided by the present systems and methods.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A stimulation circuit for a channel in a multi-channel stimulator, the stimulation circuit comprising:
    an electrical ground;
    a common supply voltage;
    first and second electrode contacts;
    first and second current sources, said first current source having a first connection and a second connection, said second current source having a third connection and a fourth connection, said first and third connections electrically connected to the common supply voltage, and said second and fourth connections electrically connected to the first electrode contact;
    third and fourth current sources, said third current source having a fifth connection and a sixth connection, said fourth current source having a seventh connection and an eighth connection, said fifth and seventh connections electrically connected to the common supply voltage, and said sixth and eighth connections electrically connected to the second electrode contact; and
    a first bypass switch configured to selectively be in one of a first and a second position, wherein, in said first position, said first bypass switch is configured to electrically connect said first electrode contact to said ground, and wherein, in a second position, said first bypass switch is configured to electrically connect said first electrode contact to said first and second current sources and permit the first and third current sources to operate together in a push-pull configuration; and
    a second bypass switch configured to selectively be in one of a first and a second position, wherein, in said first position, said second bypass switch is configured to electrically connect the second electrode contact to said ground, and wherein, in said second position, said second bypass switch is configured to electrically connect the second electrode contact to said third and fourth current sources and permit the second and fourth current sources to operate together in a push-pull configuration;
    wherein said first bypass switch is configured to be selectively placed in said first position and said second bypass switch is configured to be selectively placed in said second position to cause said channel to operate in a low compliance voltage mode in which a voltage between said first and second electrode contacts is within a first voltage range;
    wherein said first and second bypass switches are configured to both be selectively placed in said second positions to cause said channel to operate in a high compliance voltage mode in which a voltage between said first and second electrode contacts is within a second voltage range, said second voltage range greater than said first voltage range and wherein the stimulation circuit is capable of operating in both modes;
    wherein the first and second current sources provide opposite current flow in the stimulation circuit;
    wherein the third and fourth current sources provide opposite current flow in the stimulation circuit; and
    wherein the stimulation circuit is capable of operating in both the low compliance voltage mode and the high compliance voltage mode.

2. The stimulation circuit of claim 1, further comprising:
    a software programmable switch configured to control each of said current sources.

3. The stimulation circuit of claim 1, wherein the first and second bypass switches are configured to be dynamically controlled by a programmable software program.

4. The stimulation circuit of claim 1, wherein the first, second, third, and fourth current sources are configured to produce bipolar stimulation.

5. The stimulation circuit of claim 1, wherein the first electrode contact is configured to serve as an active electrode and the second electrode contact is configured to serve as an indifferent electrode.

6. The stimulation circuit of claim 1, further comprising a direct current blocking capacitor connected in series with and between the first bypass switch and the first electrode contact.

7. The stimulation circuit of claim 1, wherein said second voltage range is twice as large as said first voltage range.

* * * * *